United States Patent
Sane et al.

(10) Patent No.: US 10,133,843 B2
(45) Date of Patent: *Nov. 20, 2018

(54) SYSTEMS AND METHODS FOR STEP DISCONTINUITY REMOVAL IN REAL-TIME PCR FLUORESCENCE DATA

(71) Applicant: Roche Molecular Systems, Inc., Pleasanton, CA (US)

(72) Inventors: Aditya P. Sane, Pleasanton, CA (US); Ronald T. Kurnik, Foster City, CA (US); Jonathan M. Baldanza, Castro Valley, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1387 days.

This patent is subject to a terminal disclaimer.

(21) Appl. No.: 13/688,133

(22) Filed: Nov. 28, 2012

(65) Prior Publication Data
US 2013/0173173 A1   Jul. 4, 2013

Related U.S. Application Data

(63) Continuation of application No. 12/120,151, filed on May 13, 2008, now Pat. No. 8,374,795.

(51) Int. Cl.
  *G06F 19/22* (2011.01)
  *C12Q 1/6851* (2018.01)
  *G06F 17/18* (2006.01)

(52) U.S. Cl.
  CPC .......... *G06F 19/22* (2013.01); *C12Q 1/6851* (2013.01); *G06F 17/18* (2013.01)

(58) Field of Classification Search
  None
  See application file for complete search history.

(56) References Cited

U.S. PATENT DOCUMENTS

| | | |
|---|---|---|
| 2,997,704 A | 8/1961 | Gordon et al. |
| 2005/0159896 A1 | 7/2005 | Ishikawa et al. |
| 2007/0143070 A1 | 6/2007 | Kurnik et al. |
| 2007/0143385 A1 | 6/2007 | Kurnik et al. |
| 2007/0148632 A1 | 6/2007 | Kurnik et al. |
| 2009/0119020 A1 | 5/2009 | Kurnik et al. |

FOREIGN PATENT DOCUMENTS

CN   1588002 A   3/2005

OTHER PUBLICATIONS

Anderson, E. et al., "LAPACK Users' Guide," Third Edition, 1999, located at <http://www.netlib.org/lapack/lug/index.html>, last visited on Aug. 4, 2008, Table of Contents, 5 pages.
Burnham, K.P. et al. *Model Selection and Multimodel Inference: A Practical-Theoretic Approach*, 2nd Edition, Springer: NY, 2002, Table of Contents, 10 pages.
Moré, J.J., "The Levenberg-Marquardt Algorithm: Implementation and Theory," *Numerical Analysis*, Watson, G,A, ed., Lecture Notes in Mathematics 630, Springer-Verlag, 1977, pp. 105-116.
Press, W.H. et al. *Numerical Recipes in C: The Art of Scientific Computing*, 2nd Edition, Press Syndicate of the University of Cambridge: New York, 2002, Table of Contents, 8 pages.
Wang, S-S. et al., "Homogenous Real-Time Detection of Single-Nucleotide Polymorphisms by Strand Displacement Amplification on the BD ProbeTec ET System," *Clinc. Chem.*, 2003, vol. 49, No. 10, p. 1599.
Weissten, E.W., "Jacobian," *Mathworld—A Wolfram Web Resource*, 1999-2008, located at <http://mathworld.wolfram.com.Jacobian.html>, last accessed on Oct. 31, 2008, 4 pages.
Weisstein, E.W., "Vandermonde Matrix," *Mathworld—A Wolfram Web Resource*, 1999-2008, located at <http://mathworld.wolfram.com/VandermondeMatrix.html>, last accessed on Oct. 31, 2008, 3 pages.
Weusten, J.J.A.M. et al., "Principles of Quantitation of Viral Loads Using Nucleic Acid Sequence-Based Amplification in Combination With Homogenous Detection Using Molecular Beacons," *Nucleic Acids Research*, 2002, vol. 30, No. 6, p. 26.

*Primary Examiner* — Joseph Woitach
(74) *Attorney, Agent, or Firm* — Kilpatrick Townsend and Stockton LLP

(57) ABSTRACT

Systems and methods for removing jump discontinuities in growth data are provided. A first approximation to a received data set is determined by applying a non-linear regression process to a non-linear function that models the data set to determine parameters, including a step discontinuity parameter. A second approximation to the data set is also determined by applying a regression process to a second non-linear function to determine parameters, including a step discontinuity parameter, of the second function. One of the approximations is selected based on an information coefficient determined for each of the approximations. If a confidence interval for the step discontinuity parameter includes zero, no correction is made, and if includes zero, then a correction is made. For a correction, the portion of the data curve prior to the step change is replaced with appropriate portion of the selected approximation to produce a shift-corrected data set.

20 Claims, 14 Drawing Sheets

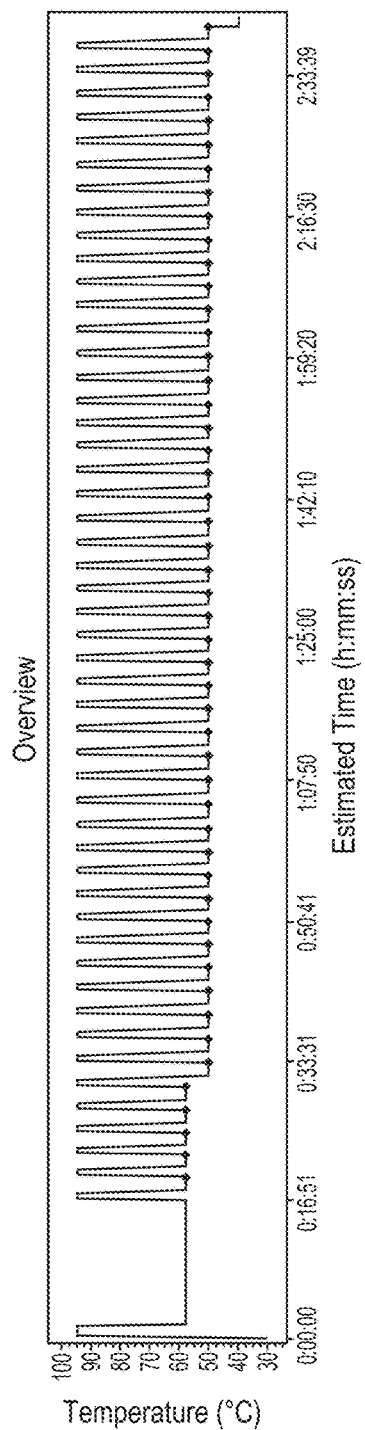
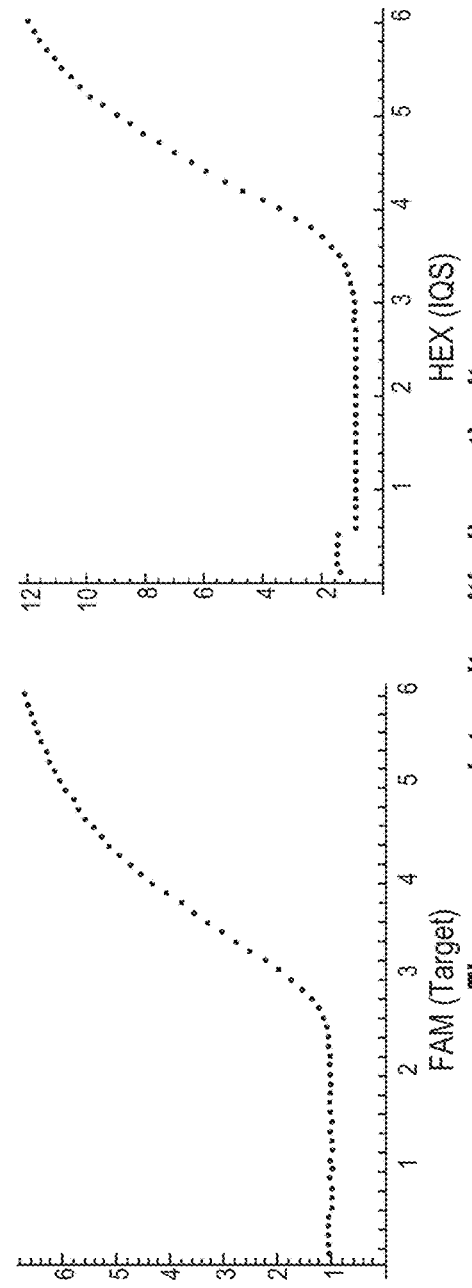
FIG. 2
FIG. 3

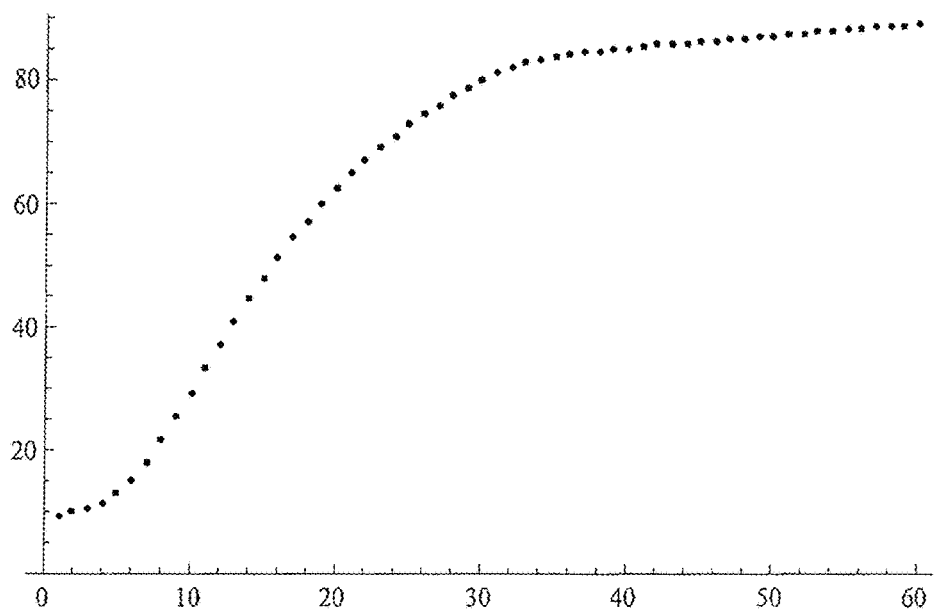
FIG. 4a: B19 Parvo target (FAM) sample with 2.9x $10^{11}$ IU/ml concentration
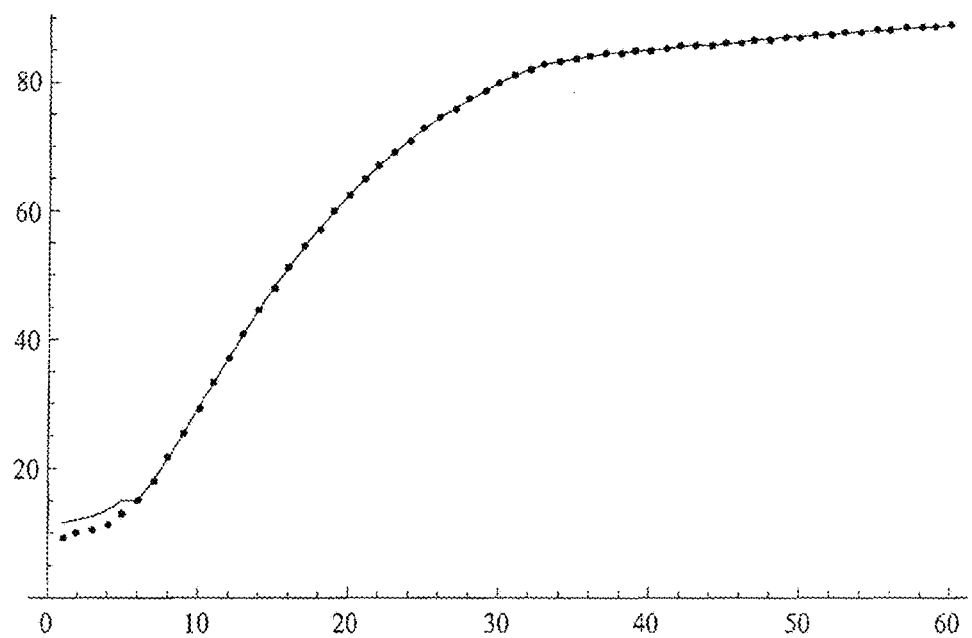
FIG. 4b: AMPLILINK® 3.1 processed data of FIG. 4a FIG. 7: Double sigmoid decomposition
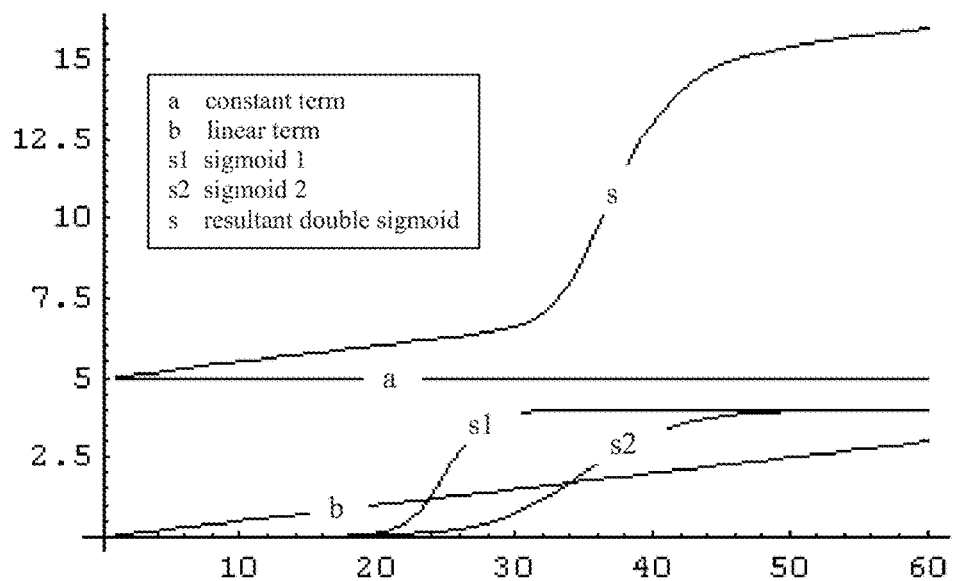
FIG. 8: The parameters of a sigmoid
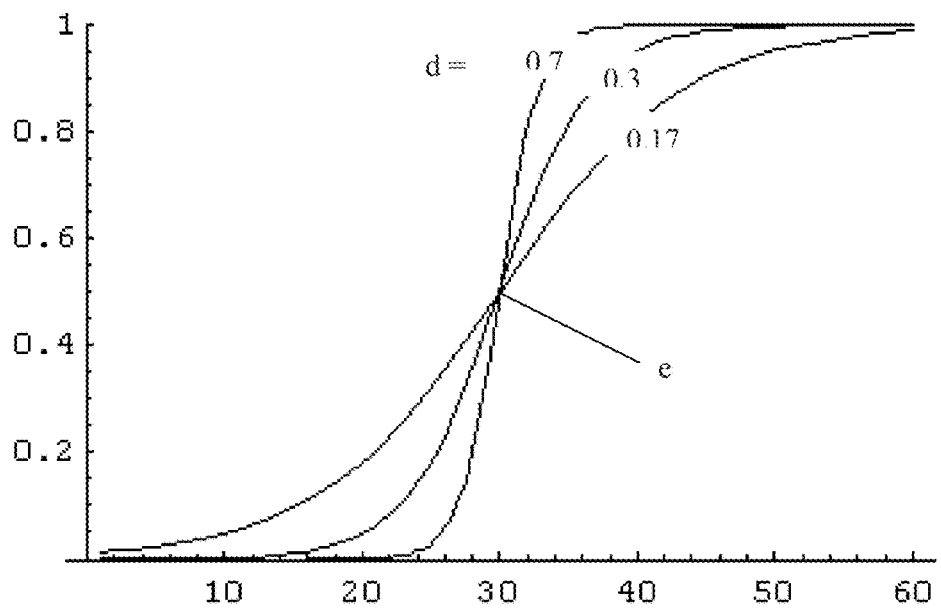

FIG. 9: Initial parameters shapes
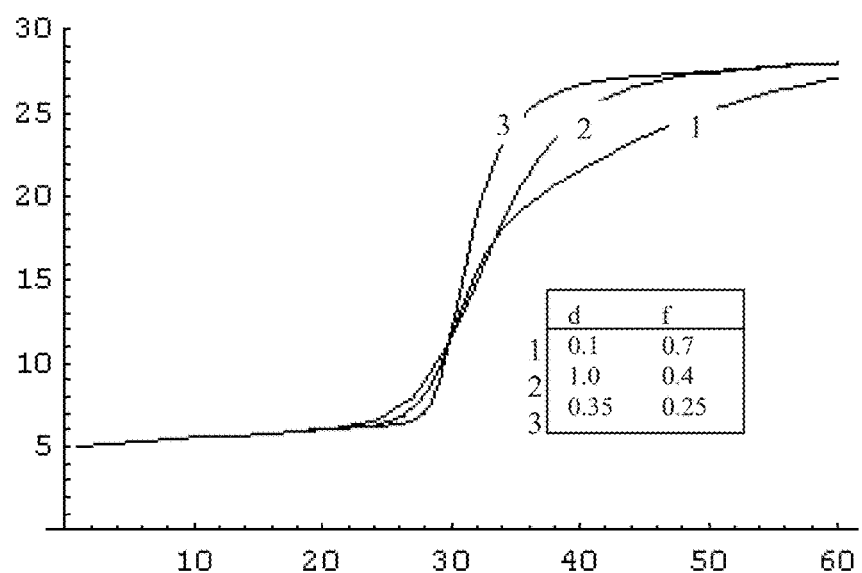

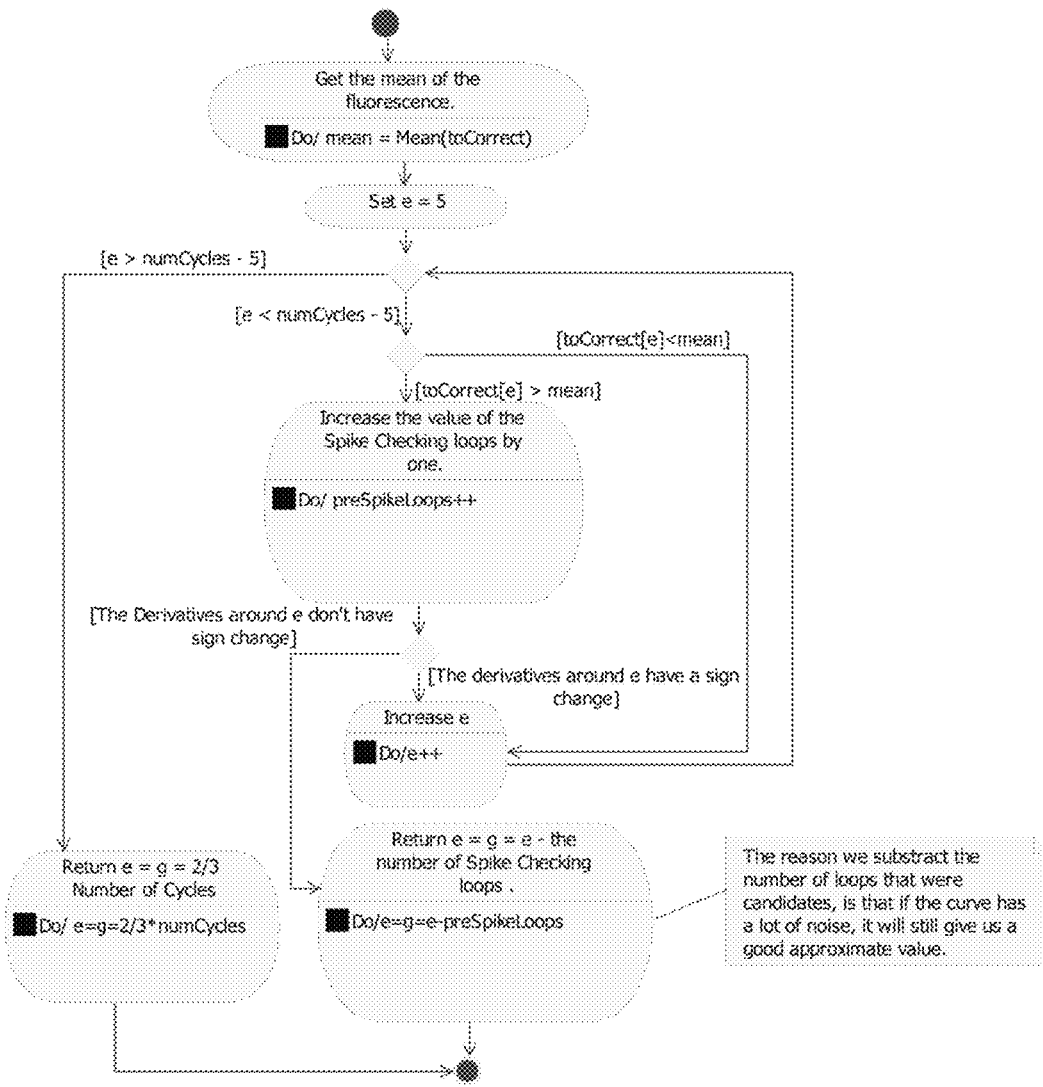
FIG. 10: Parameter e and g calculation flowchart

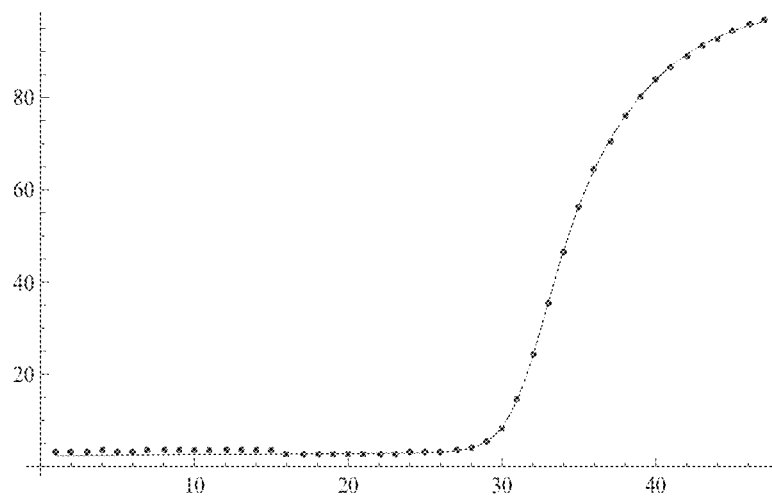
FIG 12: Case 1 illustration
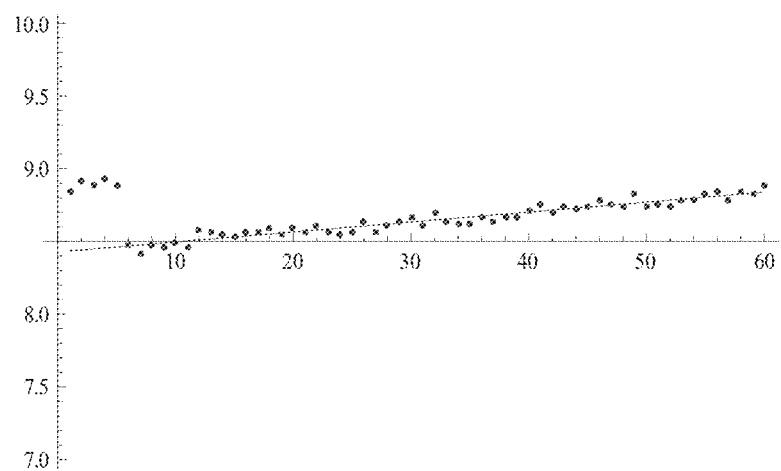
FIG. 13: Case 2 illustration

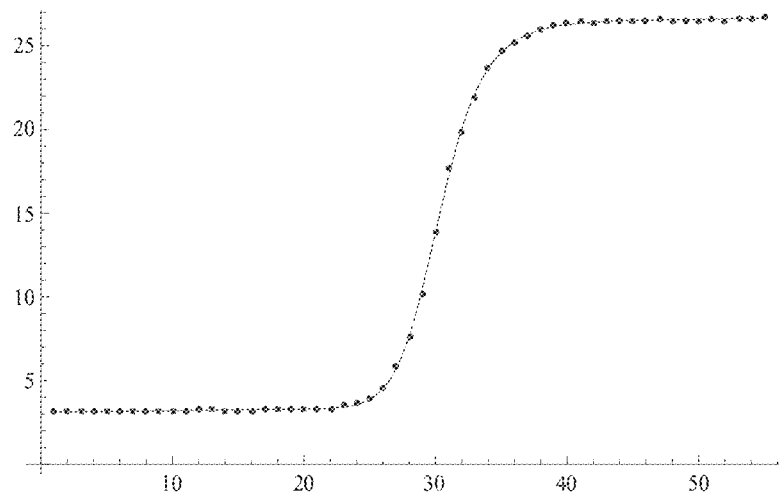
FIG. 14: Case 3 illustration
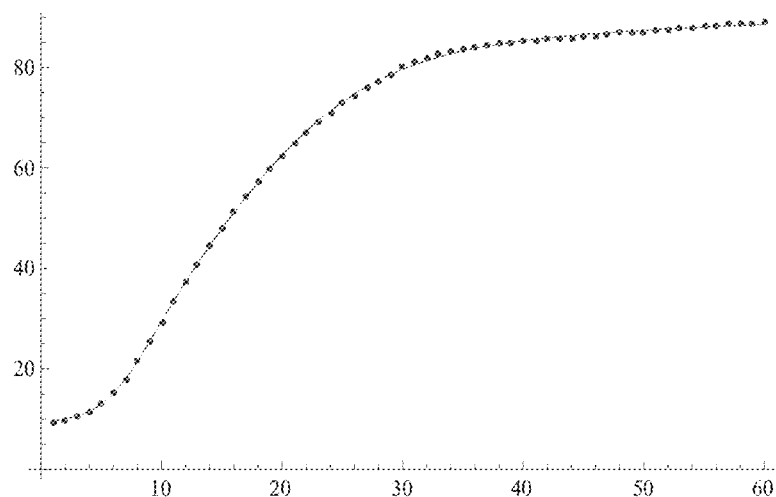
FIG. 15: Case 4 illustration

SYSTEMS AND METHODS FOR STEP DISCONTINUITY REMOVAL IN REAL-TIME PCR FLUORESCENCE DATA

CROSS-REFERENCE TO RELATED APPLICATION

The present application is a continuation of U.S. patent application Ser. No. 12/120,151, filed May 13, 2008, entitled "SYSTEMS AND METHODS FOR STEP DISCONTINUITY REMOVAL IN REAL-TIME PCR FLUORESCENCE DATA," the disclosures of which are herein fully incorporated by reference for all purposes.

BACKGROUND OF THE INVENTION

The present invention relates generally to Polymerase Chain Reaction systems, and more particularly to systems and methods for removing step discontinuities in Polymerase Chain Reaction data.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process.

A typical real-time PCR curve is shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which only emit fluorescence signals when they are bound to the target nucleic acid or in certain cases also by means of fluorescent dyes that bind to double-stranded DNA.

The fluorescence dyes used in real-time PCR are temperature sensitive. The thermal-cycling profile may include changing the annealing temperature. The change in annealing temperature manifests as a discontinuity in the fluorescence read-out magnitude. FIG. 2 shows an illustrative case where a change in annealing temperature can be seen after cycle 6.

The fluorescence data read-out corresponding to an experiment conducted using the profile of FIG. 2 is shown in FIG. 3. It can be clearly seen in the HEX channel that a discontinuity is present between cycle 5 and 6. FIG. 3 is taken from a B19 Parvo-virus sample with $10^4$ IU/ml concentration. The FAM dye being less sensitive to temperature has a jump discontinuity of a lower magnitude than the HEX dye.

However, if the concentration of the target increases, it is possible that the discontinuity may not be reflected in fluorescence data. For example, considering a B19 Parvo-virus sample with a concentration of $2.9 \times 10^{11}$ IU/ml, the discontinuity is not seen in FIG. 4a even though there was a change in annealing temperature after cycle 5.

Some current PCR systems implement methods for removal of a step discontinuity due to changes in the annealing temperature. Such systems typically require assay specific input parameters for the cycle number corresponding to the change in annealing temperature and the maximum fluorescence change expected. Such methods have a number of limitations. First, they are unable to handle high titer samples. This can be seen in FIG. 4b, where the B19 Parvo sample at $2.9 \times 10^{11}$ IU/ml concentration has been incorrectly handled by such a system. Second, such methods may only handle a small maximum (e.g., five) absolute fluorescence units change at the point of discontinuity. It has been observed in multiple assays that the magnitude of fluorescence change at the discontinuity varies widely. Setting up an assay specific input to indicate maximum change is difficult to optimize Third, such methods may be unable to handle fluorescence data where the baseline drift is high. In such cases, the correction provided may be inadequate. Fourth, if a spike happens to be present at a distance of one cycle or less from the cycle number corresponding to the change in annealing temperature, then the correction provided has been known to cause changes in reported result concentrations; i.e., a wrong result.

Therefore it is desirable to provide systems and methods for processing sigmoid-type or growth curves, and PCR curves in particular, which overcome the above and other problems. In particular, the systems and methods should implement temperature step correction in a manner that is reliable and robust.

BRIEF SUMMARY

The present invention provides systems and methods for correcting PCR data for temperature shifts that may occur during the PCR process.

Embodiments of the invention remove a jump discontinuity in fluorescence of real-time polymerase chain reaction data. The presence of the discontinuity may cause incorrect result calculation and is hence recommended to be removed. Depending on the initial copy number of the target, the discontinuity in the fluorescence may be absent at high concentration levels. The confidence region of an eight parameter nonlinear model is used to accurately estimate the data. The method overcomes difficulties in prior methods for removal of the discontinuity at all concentration levels.

In one embodiment, a first approximation to a curve that fits a received PCR data set is determined by applying a non-linear regression process to a non-linear function that models the data set to determine parameters, including a step discontinuity parameter, of the non-linear function. One example of a non-linear function is a double sigmoid equation. A second approximation to a curve that fits the PCR data set is also determined by applying a regression process to a second non-linear function to determine parameters, including a step discontinuity parameter, of the second function. One of the first or second approximations is then selected based on an information coefficient determined for each of the first and second approximations. If a confidence interval calculated for the step discontinuity parameter includes the value zero (e.g., the confidence interval spans a range that includes the value 0 (e.g., −1 to 1)), no step correction is made. If the confidence interval does not include the value zero, then a step correction is made. If a step correction is made, the portion of the data curve prior to the step change is replaced with appropriate portion of the selected approximation to produce a shift-corrected data set. In certain aspects, if the approximation does not satisfy a goodness of fit criterion, no step correction is made. The shift-corrected data set is returned and may be displayed or otherwise used for further processing.

According to one embodiment, a method is provided for automatically removing a step discontinuity in data representing a growth process. The method typically includes receiving a dataset representing a growth process, the dataset including a plurality of data points, each data point having a pair of coordinate values, and calculating a first approximation of a curve that fits the dataset by applying a non-linear regression process to a first non-linear function to determine parameters of the first function, the parameters including a step discontinuity parameter. The method also typically includes calculating a second approximation of a curve that fits the dataset by applying a second regression process to a second non-linear function to determine parameters of the second function, the parameters of the second function including a step discontinuity parameter, determining an information coefficient for each of the first and second approximations, and selecting one of the approximations based on the information coefficient. The method also typically includes determining a confidence interval of the step discontinuity parameter for the selected approximation, and if the confidence interval does not include the value zero (e.g., the confidence interval spans a range that does not include the value 0), replacing a portion of the dataset with the selected approximation with the corresponding step discontinuity parameter set to zero.

According to another embodiment, a computer-readable medium including code for controlling a processor to automatically remove a step discontinuity in a dataset representing a growth curve is provided. The code typically includes instructions to receive a dataset representing a growth process, the dataset including a plurality of data points, each data point having a pair of coordinate values, and to calculate a first approximation of a curve that fits the dataset by applying a non-linear regression process to a first non-linear function to determine parameters of the first function, the parameters including a step discontinuity parameter. The code also typically includes instructions to calculate a second approximation of a curve that fits the dataset by applying a second regression process to a second non-linear function to determine parameters of the second function, the parameters of the second function including a step discontinuity parameter, to determine an information coefficient for each of the first and second approximations, and to select one of the approximations based on the information coefficient. The code also typically includes instructions to determine a confidence interval of the step discontinuity parameter for the selected approximation, and to replace a portion of the dataset with the selected approximation with the corresponding step discontinuity parameter set to zero if the confidence interval does not include the value zero.

According to yet another embodiment, A kinetic Polymerase Chain Reaction (PCR) system is provided that typically includes a kinetic PCR analysis module that generates a PCR dataset representing a kinetic PCR amplification curve, the dataset including a plurality of data points, each having a pair of coordinate values, and an intelligence module. The intelligence module is typically adapted to process the PCR dataset to automatically remove a step discontinuity in the dataset, by calculating a first approximation of a curve that fits the dataset by applying a non-linear regression process to a first non-linear function to determine parameters of the first function, the parameters including a step discontinuity parameter, and calculating a second approximation of a curve that fits the dataset by applying a second regression process to a second non-linear function to determine parameters of the second function, the parameters of the second function including a step discontinuity parameter. The intelligence module is also typically adapted to determine an information coefficient for each of the first and second approximations, to select one of the approximations based on the information coefficient, to determine a confidence interval of the step discontinuity parameter for the selected approximation, and, if the confidence interval does not include the value zero, to replace a portion of the dataset with the selected approximation with the corresponding step discontinuity parameter set to zero.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 2 shows an illustrative case where a change in annealing temperature can be seen after cycle 6.

FIG. 3 illustrates a PCR amplification curve, in FEM and HEX channels, taken from a B19 Parvo-virus sample with $10^4$ IU/ml concentration.

FIG. 4A illustrates a PCR amplification curve showing that if the concentration of the target increases, it is possible that the discontinuity is not reflected in fluorescence data. FIG. 4B illustrates a PCR amplification curve where a discontinuity has been incorrectly handled.

FIG. 7 illustrates a decomposition of the double sigmoid equation including parameters a-g. Parameters a-g define the shape and position of a double sigmoid curve.

FIG. 8 shows the influence of parameter (d) on the curve and the position of (e), the x value of the inflexion point. All curves in FIG. 8 have the same parameter values except for parameter d.

FIG. 9 shows an example of the three curve shapes for the different parameter sets.

FIG. 10 illustrates a process for determining the value of double sigmoid equation parameters (e) and (g) according to one aspect.

FIG. 12 illustrates an IQS (HEX channel) fluorescence data from a CAP/CTM HIV Monitor assay; the raw fluorescence data is shown as dots and the corrected data shown as a solid line.

FIG. 13 illustrates fluorescent data of a B19 Parvo-virus target channel (FAM Channel) assay (without any real target being amplified); the raw fluorescence data is shown as dots and the corrected data shown as a solid line.

FIG. 14 illustrates fluorescent data of a target of a HBV High Pure (FAM channel) assay; the raw fluorescence data is shown as dots and the corrected data shown as a solid line. This assay does not have a jump discontinuity, hence, no correction of discontinuity is required.

FIG. 15 illustrates fluorescent data of a high concentration ($2.9 \times 10^{11}$ IU/ml) B19 Parvo-virus sample (FAM channel) assay; the raw fluorescence data is shown as dots and the corrected data shown as a solid line.

DETAILED DESCRIPTION

The present invention provides systems and methods for correcting PCR amplification curves, and other growth curves, for temperature shifts that may occur during the amplification process.

One example of a temperature shift is a controlled change in the annealing temperature at a certain cycle during the assay. Typically this temperature shift occurs during a portion of the process represented by the baseline region. This temperature change causes a subsequent shift in the fluorescent signal at the cycle number where the shift occurred. The cycle where the temperature shift occurred will be referred to herein as the CAC, for cycle of annealing change.

In one embodiment, a first approximation to a curve that fits a PCR data set is determined by applying a non-linear regression process to a non-linear function that models the data set to determine parameters, including a step discontinuity parameter, of the non-linear function. One example of a non-linear function is a double sigmoid equation as described in more detail below. A second approximation to a curve that fits the PCR data set is also determined by applying a regression process to a second non-linear function to determine parameters, including a step discontinuity parameter, of the second function. One of the first or second approximations is then selected based on an information coefficient determined for each of the first and second approximations. If a confidence interval calculated for the step discontinuity parameter includes the value zero (e.g., the confidence interval spans a range that includes the value 0), no step correction is made. If the confidence interval does not include the value zero, then a step correction is made. If a step correction is made, the portion of the data curve prior to the step change is replaced with appropriate portion of the selected approximation to produce a shift-corrected data set. In certain aspects, if the approximation does not satisfy a goodness of fit criterion, no step correction is made. The shift-corrected data set is returned and may be displayed or otherwise used for further processing. For example, the shift-corrected data set can be used to determine the Ct value of the PCR assay.

Amplification Curves

Figure 1:
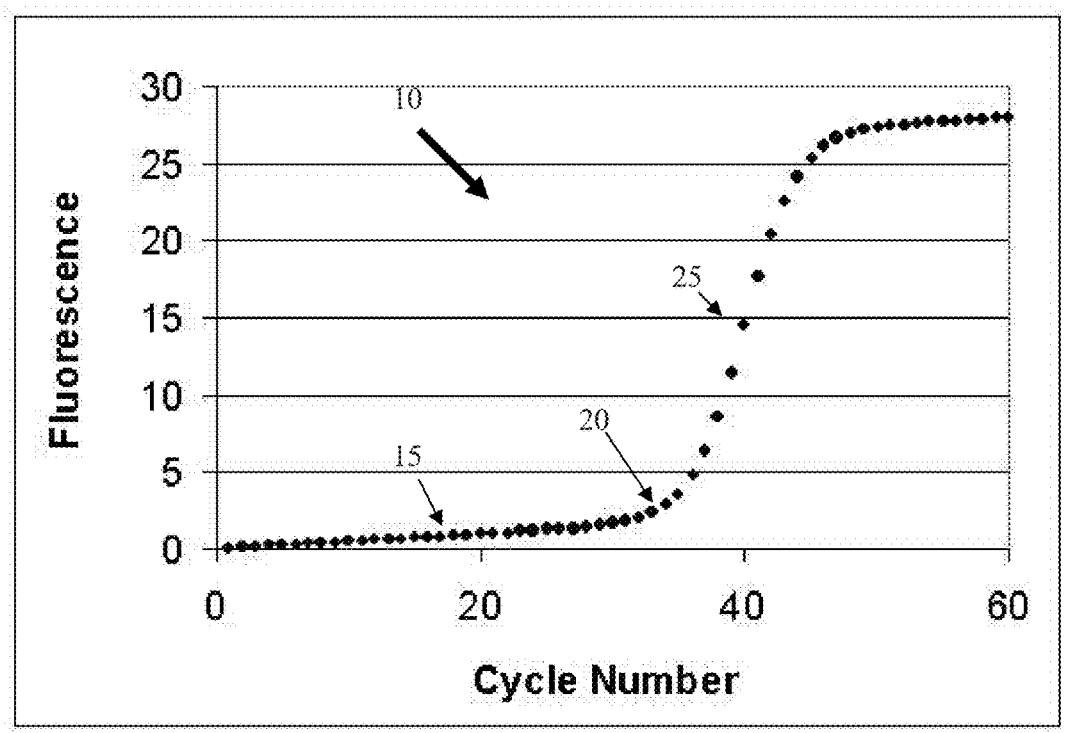
FIG. 1 illustrates an example of an amplification curve in the context of a PCR process.

One example of an amplification curve 10 in the context of a PCR process is shown in FIG. 1. As shown, the curve 10 includes a lag phase region 15, and an exponential phase region 25. Lag phase region 15 is commonly referred to as the baseline or baseline region. Such a curve 10 includes a transitional region of interest 20 linking the lag phase and the exponential phase regions. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process. In a typical PCR curve, identifying a transition point referred to as the elbow value or cycle threshold (Ct) value is useful for understanding efficiency characteristics of the PCR process.

Other processes that may provide similar sigmoid or growth curves include bacterial processes, enzymatic processes and binding processes. In bacterial growth curves, for example, the transition point of interest has been referred to as the time in lag phase, 2. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System", Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons", Nucleic Acids Research, 2002 30(6):26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, as shown in FIG. 1, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of abundance or accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

General Process

Figure 5:
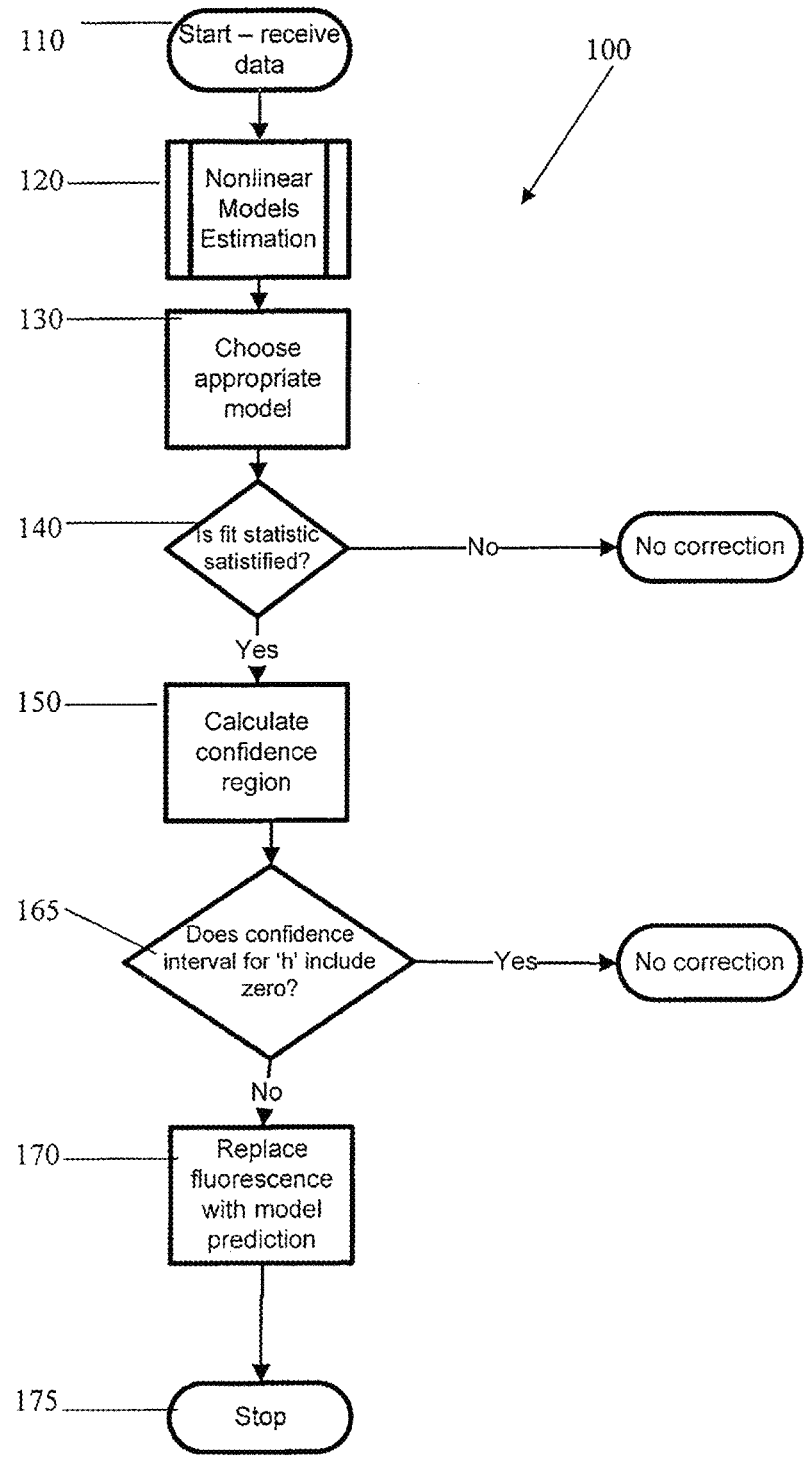
FIG. 5 illustrates one embodiment of a process for correcting for a temperature shift in a PCR amplification curve.

According to the present invention, one embodiment of a process 100 for correcting for a temperature shift of a kinetic PCR amplification curve can be described with reference to FIG. 5. In step 110, an experimental data set representing the curve is received or otherwise acquired. The cycle at which a temperature shift occurred is also identified. Typically this cycle value is known a priori, e.g., recorded by the device or instrument providing the data. Examples of plotted PCR data sets are shown in FIGS. 1, 3 and 4, where the y-axis and x-axis represent fluorescence intensity and cycle number, respectively, for a PCR curve. In certain aspects, the data set should include data that is continuous and equally spaced along an axis.

In the case where process 100 is implemented in an intelligence module (e.g., processor executing instructions) resident in a PCR data acquiring device such as a thermocycler, the data set may be provided to the intelligence module in real time as the data are being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk, portable USB drive or the like. In certain aspects, the data set includes data points having a pair of coordinate values (or a 2-dimensional vector). For PCR data, the pair of coordinate values typically represents the cycle number and the fluorescence intensity value. After the data set has been received or acquired in step 110, the data set may be further analyzed, e.g., to correct for temperature shifts during the assay.

In step 120, a first approximation is computed on the data set, e.g., from cycle 1 to the end cycle. During this step, in one embodiment, a double sigmoid function with parameters determined by a Levenberg-Marquardt (LM) regression process or other regression process is used to find an approximation of a curve representing the data set. A second approximation different than the first approximation is also computed on the data set in step 120 as will be discussed in more detail below.

According to one embodiment, the confidence region of a nonlinear model with a step function incorporated therein is used. Building on the double sigmoid model presented in U.S. patent application Ser. No. 11/533,291, titled "PCR Elbow Determination Using Curvature Analysis of a Double Sigmoid," filed Sep. 19, 2006, and U.S. patent application Ser. No. 11/861,188, titled "PCR Elbow Determination Using Quadratic Test for Curvature Analysis of a Double Sigmoid," filed Sep. 25, 2007, both of which are hereby incorporated by reference, according to one embodiment, the function specified in Equation 1 is used as the first nonlinear model:

Nonlinear model    Equation 1

$$a + b \cdot x + \frac{c}{(1 + \exp(-d \cdot (x - e)))(1 + \exp(-f \cdot (x - g)))} + h \cdot (\text{UnitStep}(x) - \text{UnitStep}(x - cac))$$

In Equation 1, {a, b, c, d, e, f, g, h} are the model coefficients and cac is the cycle number where the annealing temperature changes. The cac value is known and is provided by the system. The coefficient 'h' represents the magnitude of the jump discontinuity. A nonlinear regression method (for example, the Levenberg-Marquardt method, as will be detailed below) is used to derive the coefficients corresponding to the nonlinear model. The nonlinear regression typically requires a set of initial coefficients for proper global convergence that is application specific. Details of the regression process and parameter determination are shown in more detail below.

In one embodiment, the UnitStep function as defined in Equation 2 is used:

UnitStep function    Equation 2

$$\text{UnitStep}(x) = \begin{cases} 1 & x \geq 0 \\ 0 & x < 0 \end{cases}$$

According to one embodiment, the second model is specified in Equation 3:

$a+b \cdot x+h \cdot (\text{UnitStep}(x)- \text{UnitStep}(x-cac))$    Equation 3 Additional nonlinear model In one aspect, the second nonlinear model is used to accurately represent fluorescence data generated from reaction wells with no target. A nonlinear regression method (for example, a least squares QRD fit or other regression method) is used to derive the coefficients corresponding to the second nonlinear model.

According to one embodiment, in step 130, a selection is made between the model specified in equation 1 and the model specified in equation 3. The selection between the model specified in Equation 1 and the model specified in Equation 3 is made, in certain aspects, using a non-parametric information theory based approach. In one embodiment, a Modified Akaike Information Coefficient (aic), as defined in Equation 4, is calculated for each of the nonlinear regression models (equations 1 and 2). In this embodiment, the regression model with the lowest coefficient is assumed to be the best fit. In one aspect, a bias value is subtracted from the model specified by Equation 3. This bias allows samples with no growth to be detected accurately. The bias value may range from 0 (no bias) to about 50. In certain aspects, a bias of about 10 is subtracted.

Modified Akaike's Information Coefficient    Equation 4

$$aic = n \cdot \ln\left(\frac{\|\hat{y} - y\|^2}{n}\right) + 2 \cdot m + \frac{2 \cdot m \cdot (m + 1)}{n - m - 1}$$

In Equation 4, ($\hat{y}$–y) is the prediction residual, n is number of fluorescence acquisition cycles, and m is the degrees of freedom of the model (e.g., 8 for Equation 1 and 3 for Equation 3).

According to one embodiment, in step 140, a goodness-of-fit statistic (e.g., $R^2$) is calculated to verify that the model expressions actually match the fluorescence data. If this statistic is outside a predefined range, then the model has not converged and no discontinuity correction of fluorescence data is performed. For example, in one aspect, if $R^2<0.8$ then convergence is not achieved.

The $R^2$ value is computed with respect to the raw curve (fluorescence data) and the estimated model. In one aspect, an equation to compute the $R^2$ values is given as follows:

$$r^2 = 1 - \frac{\sum_{i=0}^{n-1}(f(x_i) - y_i)^2}{\sum_{i=0}^{n-1}(y_i - \bar{y})^2},$$

where y represents the raw data curve, f(x) represents the modeled curve, $\bar{y}$ represents the raw data curve mean value, and n represents the length (in cycles) of the raw data curve.

According to one embodiment, in step 150, a confidence interval of the h coefficient is calculated from Equation 1 or Equation 3, depending on which is selected, at a given confidence level (e.g., between 90 to 99.9%, such as 95%). If this confidence interval includes the value zero, then the model has coefficient h as an over-determined parameter. In such cases, a discontinuity in data is not identified and discontinuity correction of fluorescence is not required. The confidence interval computation for the h coefficient depends from the model chosen and the model standard error. In certain aspects, the width of the confidence interval is determined as follows:

$$ci = 1.96 \cdot \sqrt{H_h^{-1} \cdot \text{stdError}},$$

where 1.96 represents a confidence at 95%, $H^1$ represents the inverse of the Hessian matrix for the h coefficient, and stdError represents the standard error of the chosen model. The Hessian matrix is computed as follows:

$$H = J^T \cdot J,$$

where J is the Jacobian matrix and $J^T$ the Jacobian transpose matrix. The Jacobian is the evaluation of the first partial derivative for each model coefficient at every fluorescence cycle. The standard error is computed as follows:

$$stdError = \frac{\sum_{i=0}^{n-1}(f(x_i) - y_i)^2}{n-2},$$

where y represents the raw curve, f(x) represents the modeled curve, and n represents the length of the curve. The lower and upped limits of the confidence interval are computed as h±ci, where the value of h is given by the estimation model.

It should be appreciated that steps 140 and 150 (including 165) are interchangeable and that both are optional.

According to one embodiment, in step 170, a step- or shift-corrected data set is produced. In one aspect, the raw fluorescence intensity data values are replaced with values obtained from the selected model by setting coefficient h equal to zero. In one aspect, the replacement is performed for the cycles that occur before the change in annealing temperature; this effectively eliminates the jump discontinuity and ensures smooth transition. In one aspect, the replacement is performed beginning with the first cycle up to and including the cycle after the cycle where the change in annealing temperature occurs, e.g., cycle 1 to cac+1.

In step 175, the modified, shift-corrected data set is returned, e.g., for display or further processing. For example, the corrected curve may be processed to determine the Ct value, and the result (shift-corrected data and/or Ct value) may be returned, for example to the system that performed the analysis, or to a separate system that requested the analysis. Graphical displays may be rendered with a display device, such as a monitor screen or printer, coupled with the system that performed the analysis of FIG. 5, or data may be provided to a separate system for rendering on a display device. The Ct value may be determined according to various methods using the corrected data set. For example, in one aspect, the teachings of U.S. patent application Ser. Nos. 11/316,315 and 11/349,550, each of which is hereby incorporated by reference, can be used to determine the Ct value.

In one embodiment, equation 1 is provided with three different starting conditions to derive 3 sets of coefficients, and equation 3 is provided with a single set of starting conditions to derive a single set of coefficients. In this embodiment, equation 4 is processed using the four derived sets of coefficients to determine the model with the lowest aic value as described above. It will be appreciated that different starting conditions may be used for each of the non-linear equations used to model the process. In certain aspects, the starting conditions are determined empirically.

LM Regression Process

Figure 6:
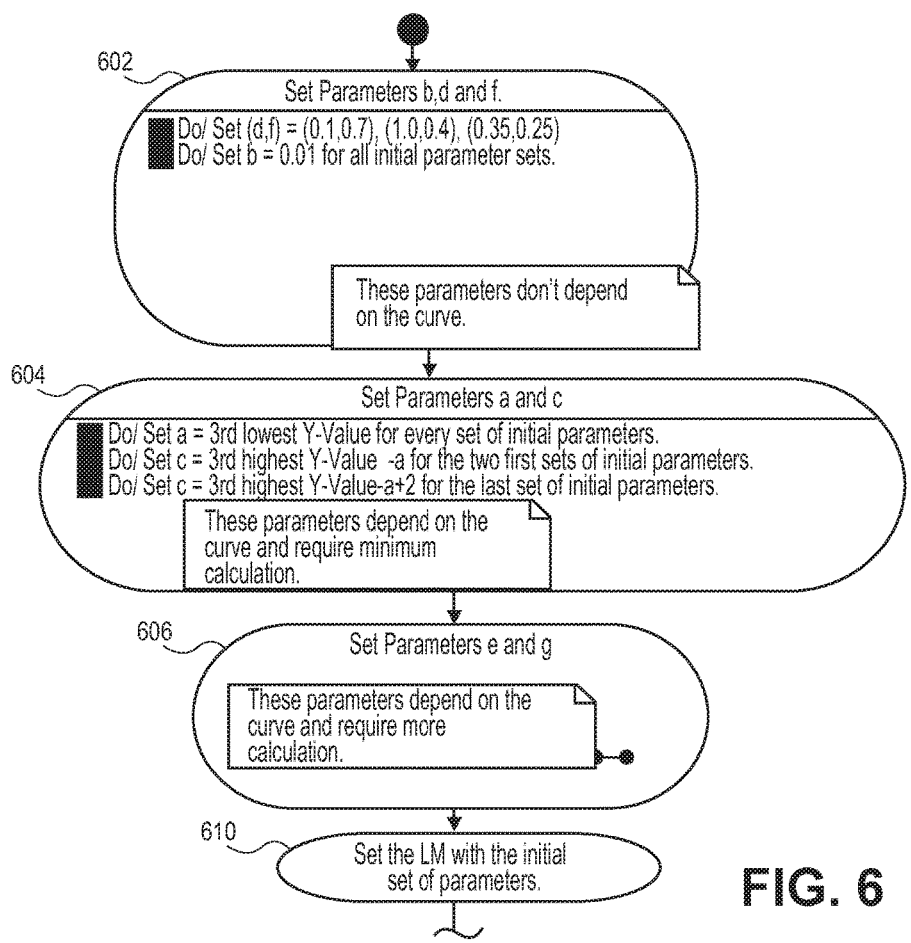
FIG. 6 illustrates a detailed process flow for a spike identification and replacement process according to one embodiment of the present invention.
Figure 6:
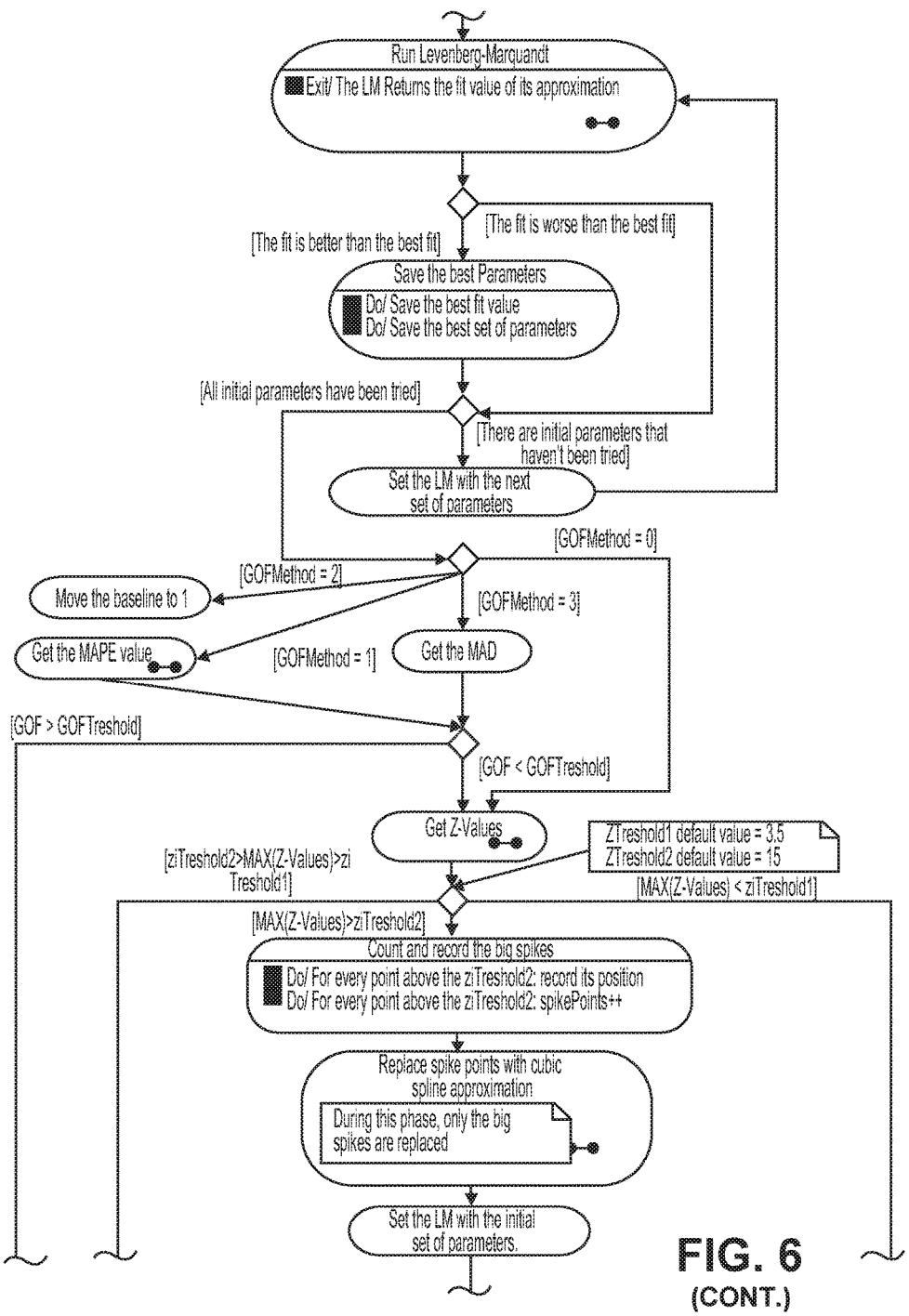
Figure 6:
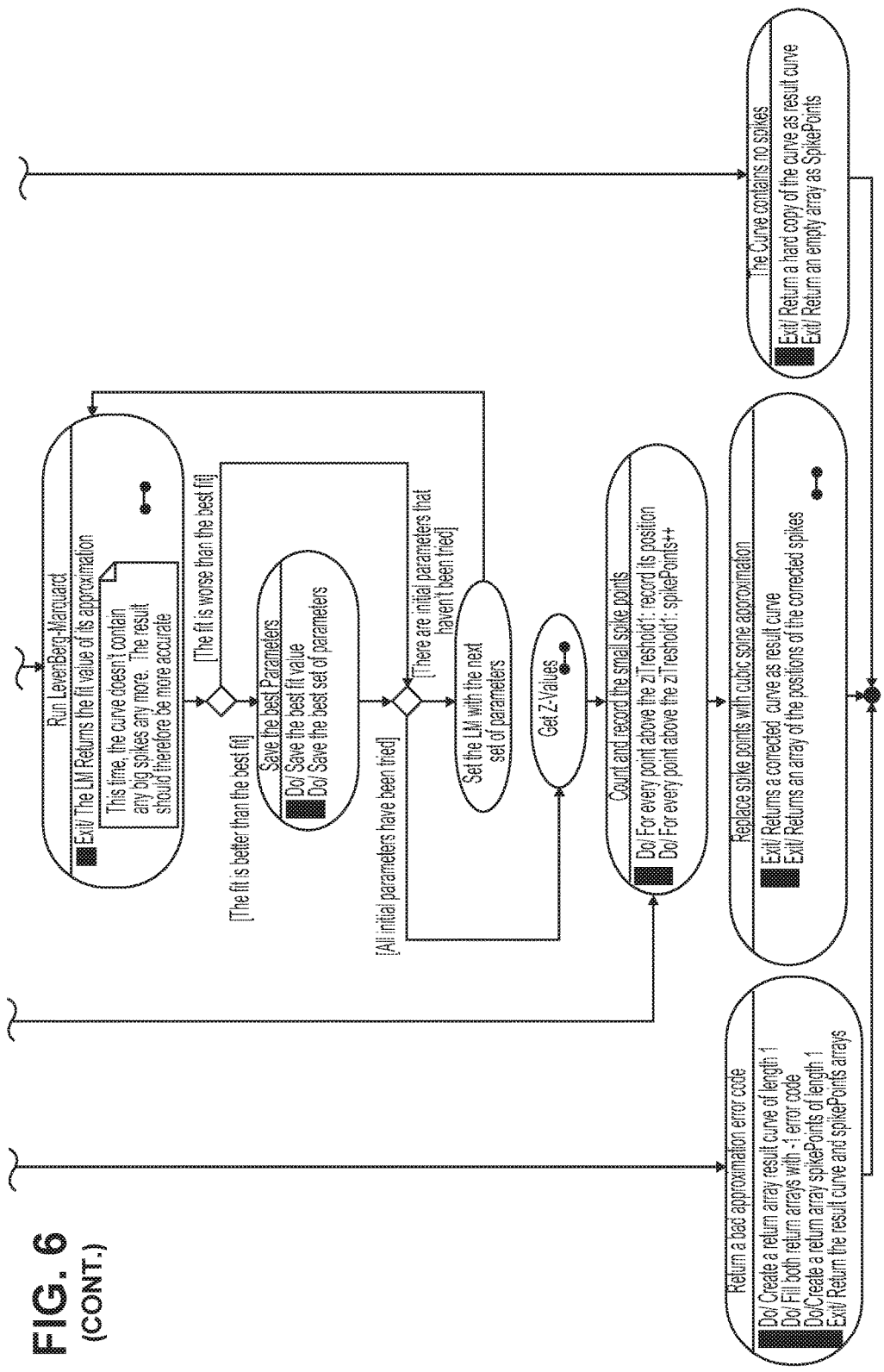

Steps 502 through 524 of FIG. 6 illustrate a process flow for approximating the curve of a data set and determining the parameters of a fit function. In one embodiment, a Levenberg-Marquardt (LM) method is used to calculate a robust curve approximation of a data set on the curve points. The LM method is a non-linear regression process; it is an iterative technique that minimizes the distance between a non-linear function and a data set. The process behaves like a combination of a steepest descent process and a Gauss-Newton process: when the current approximation doesn't fit well it behaves like the steepest descent process (slower but more reliable convergence), but as the current approximation becomes more accurate it will then behave like the Gauss-Newton process (faster but less reliable convergence).

In general, the LM regression method includes an algorithm that requires various inputs and provides output. In one aspect, the inputs include a data set to be processed, a function that is used to fit the data, and an initial guess for the parameters or variables of the function. The output includes a set of parameters for the function that minimizes the distance between the function and the data set.

According to one embodiment, the fit function is a double sigmoid of the form:

$$f(x) = a + bx + \frac{c}{(1 + \exp^{-d(x-e)})(1 + \exp^{-f(x-g)})}. \quad (5)$$

The choice of this equation as the fit function is based on its flexibility and its ability to fit the different curve shapes that a typical PCR curve or other growth curve may take. One skilled in the art will appreciate that variations of the above fit function or other fit functions may be used as desired. For example, equation 1 is used in one embodiment.

The double sigmoid equation (5) has 7 parameters: a, b, c, d, e, f and g, whereas equation 1 has 8 parameters: a, b, c, d, e, f, g and h. The equation can be decomposed into a sum of a constant, a slope and a double sigmoid. The double sigmoid itself is the multiplication of two sigmoids. FIG. 7 illustrates a decomposition of the double sigmoid equation (5). The parameters d, e, f and g determine the shape of the two sigmoids. To show their influence on the final curve, consider the single sigmoid:

$$\frac{1}{1 + \exp^{-d(x-e)}}, \quad (6)$$

where the parameter d determines the "sharpness" of the curve and the parameter e determines the x-value of the inflexion point. FIG. 8 shows the influence of the parameter d on the curve and of the parameter e on the position of the x value of the inflexion point. Table 1, below, describes the influence of the parameters on the double sigmoid curve.

TABLE 1

| Double sigmoid parameters description | |
|---|---|
| Parameter | Influence on the curve |
| a | Value of y at x = 0 |
| b | baseline and plateau slope |
| c | AFI of the curve |
| d | "sharpness" of the first sigmoid (See FIG. 9) |
| e | position of the inflexion point of the first sigmoid (See FIG. 10) |
| f | "sharpness" of the second sigmoid |
| g | position of the inflexion point of the second sigmoid |

In one aspect, the "sharpness" parameters d and f of the double sigmoid equation should be constrained in order to prevent the curve from taking unrealistic shapes. Therefore, in one aspect, any iterations where d<−1 or d>1.1 or where f<−1 or f>1.1 is considered unsuccessful. In other aspects, different constraints on parameters d and f may be used.

Because the Levenberg-Marquardt algorithm is an iterative algorithm, an initial guess for the parameters of the function to fit is typically needed. The better the initial guess, the better the approximation will be and the less likely it is that the algorithm will converge towards a local minimum. Due to the complexity of the double sigmoid function and the various shapes of PCR curves or other growth curves, one initial guess for every parameter may not be sufficient to prevent the algorithm from sometimes converging towards local minima Therefore, in one aspect, multiple (e.g., three or more) sets of initial parameters are input and the best result is kept. In one aspect, most of the parameters are held constant across the multiple sets of parameters used; only parameters c, d and f may be different for each of the multiple parameter sets. FIG. 9 shows an example of the three curve shapes for the different parameter sets. The choice of these three sets of parameters is indicative of three possible different shapes of curves representing PCR data. It should be understood that more than three sets of parameters may be processed and the best result kept.

As shown in FIG. 6, the initial input parameters of the LM method are identified in step 510. These parameters may be input by an operator or calculated. According to one aspect, the parameters are determined or set according to steps 502, 504 and 506 as discussed below.

Calculation of Initial Parameter (a):
The parameter (a) is the height of the baseline; its value is the same for all sets of initial parameters. In one aspect, in step 504 the parameter (a) is assigned the 3rd lowest y-axis value, e.g., fluorescence value, from the data set. This provides for a robust calculation. In other aspects, of course, the parameter (a) may be assigned any other fluorescence value as desired such as the lowest y-axis value, second lowest value, etc.

Calculation of Initial Parameter (b):
The parameter (b) is the slope of the baseline and plateau. Its value is the same for all sets of initial parameters. In one aspect, in step 502 a static value of 0.01 is assigned to (b) as ideally there shouldn't be any slope. In other aspects, the parameter (b) may be assigned a different value, for example, a value ranging from 0 to about 0.5. In one aspect, the value (b) represents the baseline slope from CAC+1 to the end of the baseline.

Calculation of Initial Parameter (c):
The parameter (c) represents the height of the plateau minus the height of the baseline, which is denoted as the absolute fluorescence increase, or AFI. In one aspect, for the first set of parameters, c=AFI+2, whereas for the last two parameters, c=AFI. This is shown in FIG. 9, where for the last two sets of parameters, c=AFI. For the first set of parameters, c=AFI+2. This change is due to the shape of the curve modeled by the first set of parameters, which doesn't have a plateau.

Calculation of parameters (d) and (f):
The parameters (d) and (f) define the sharpness of the two sigmoids. As there is no way of giving an approximation based on the curve for these parameters, in one aspect three static representative values are used in step 502. It should be understood that other static or non-static values may be used for parameters (d) and/or (f). These pairs model the most common shapes on PCR curves encountered. Table 2, below, shows the values of (d) and (f) for the different sets of parameters as shown in FIG. 9.

TABLE 2

Values of parameters d and f

| Parameter set number | Value of d | Value of f |
|---|---|---|
| 1 | 0.1 | 0.7 |
| 2 | 1.0 | 0.4 |
| 3 | 0.35 | 0.25 |

Calculation of parameters (e) and (g):
In step 506, the parameters (e) and (g) are determined. The parameters (e) and (g) define the inflexion points of the two sigmoids. In one aspect, they both take the same value across all the initial parameter sets. Parameters (e) and (g) may have the same or different values. To find an approximation, in one aspect, the x-value of the first point above the mean of the intensity, e.g., fluorescence, (which isn't a spike) is used. A process for determining the value of (e) and (g) according to this aspect is shown in FIG. 10 and discussed below. A more detailed description of the process for determining the value of the parameters (e) and (g), and other parameters, according to this aspect can be found in U.S. patent application Ser. No. 11/316,315, filed on Dec. 20, 2005, the disclosure of which was previously incorporated by reference in its entirety.

With reference to FIG. 10, initially, the mean of the curve (e.g., fluorescence intensity) is determined Next, the first data point above the mean is identified. It is then determined whether:

a. that point does not lie near the beginning, e.g., within the first 5 cycles, of the curve;
b. that point does not lie near the end, e.g., within the 5 last cycles, of the curve; and
c. the derivatives around the point (e.g., in a radius of 2 points around it) do not show any change of sign. If they do, the point is likely to be a spike and should therefore be rejected.

In another embodiment, only the fluorescence values for cycles after the cac cycle are considered in determining coefficients (e) and (g). Thus, to find an approximation, the x-value of the first point above the mean of the intensity, e.g., fluorescence, (which isn't a spike) for cycles cac to the last cycle is used. First the mean of the curve (for cycles cac to the last cycle) is determined, and the first point above the mean is determined. If no such point is found, two-thirds of the raw curve length is then considered in one aspect.

Table 3, below, shows examples of initial parameter values as used in FIG. 9 according to one aspect.

TABLE 3

Initial parameters values:

| Initial parameter set number | 1 | 2 | 3 |
|---|---|---|---|
| Value of a | $3^{rd}$ lowest fluorescence value | $3^{rd}$ lowest fluorescence value | $3^{rd}$ lowest fluorescence value |
| Value of b | 0.01 | 0.01 | 0.01 |
| Value of c | $3^{rd}$ highest fluorescence value − a + 2 | $3^{rd}$ highest fluorescence value − a | $3^{rd}$ highest fluorescence value − a |
| Value of d | 0.1 | 1.0 | 0.35 |
| Value of e | X of the first non-spiky point above the mean of the fluorescence | X of the first non-spiky point above the mean of the fluorescence | X of the first non-spiky point above themean of the fluorescence |

TABLE 3-continued

Initial parameters values:

| Initial parameter set number | 1 | 2 | 3 |
|---|---|---|---|
| Value of f | 0.7 | 0.4 | 0.25 |
| Value of g | X of the first non-spiky point above the mean of the fluorescence | X of the first non-spiky point above the mean of the fluorescence | X of the first non-spiky point above the mean of the fluorescence |

Returning to FIG. 6, once all the parameters are set in step 510, a LM process 520 is executed using the input data set, function and parameters. Traditionally, the Levenberg-Marquardt method is used to solve non-linear least-squares problems. The traditional LM method calculates a distance measure defined as the sum of the square of the errors between the curve approximation and the data set. However, when minimizing the sum of the squares, it gives outliers an important weight as their distance is larger than the distance of non-spiky data points, often resulting in inappropriate curves or less desirable curves. Therefore, according to one aspect of the present invention, the distance between the approximation and the data set is computed by minimizing the sum of absolute errors as this does not give as much weight to the outliers. In this aspect, the distance between the approximation and data is given by:

$$\text{distance} = \Sigma |y_{data} - y_{approximation}|. \quad (7)$$

As above, in one aspect, each of the multiple (e.g., three) sets of initial parameters are input and processed and the best result is kept as shown in steps 522 and 524, where the best result is the parameter set that provides the smallest or minimum distance in equation (7). In one aspect, most of the parameters are held constant across the multiple sets of parameters; only c, d and f may be different for each set of parameters. It should be understood that any number of initial parameter sets may be used.

Figure 11:
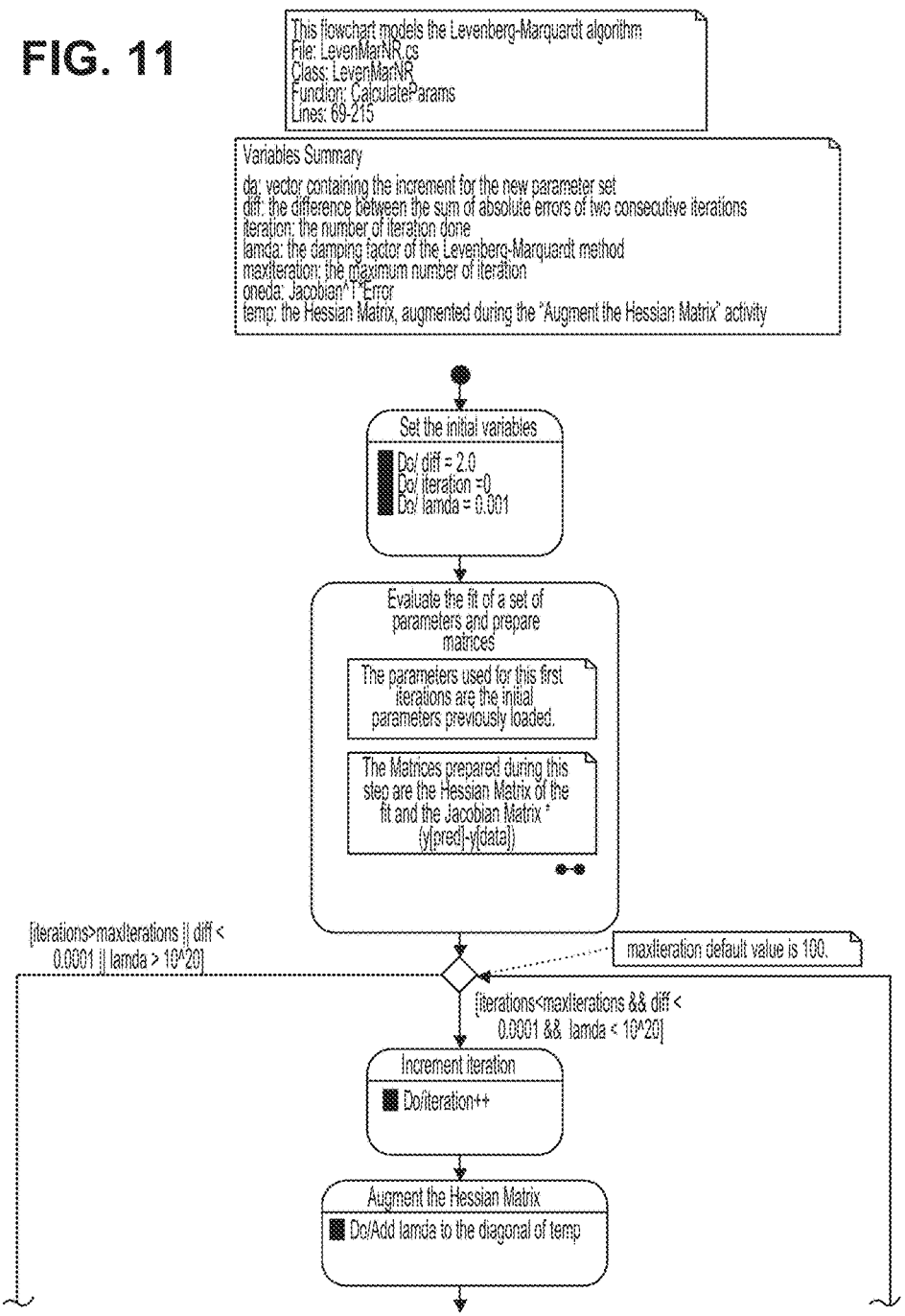
FIG. 11 illustrates a process flow of a Levenberg-Marquardt regression process for an initial set of parameters.
Figure 11:
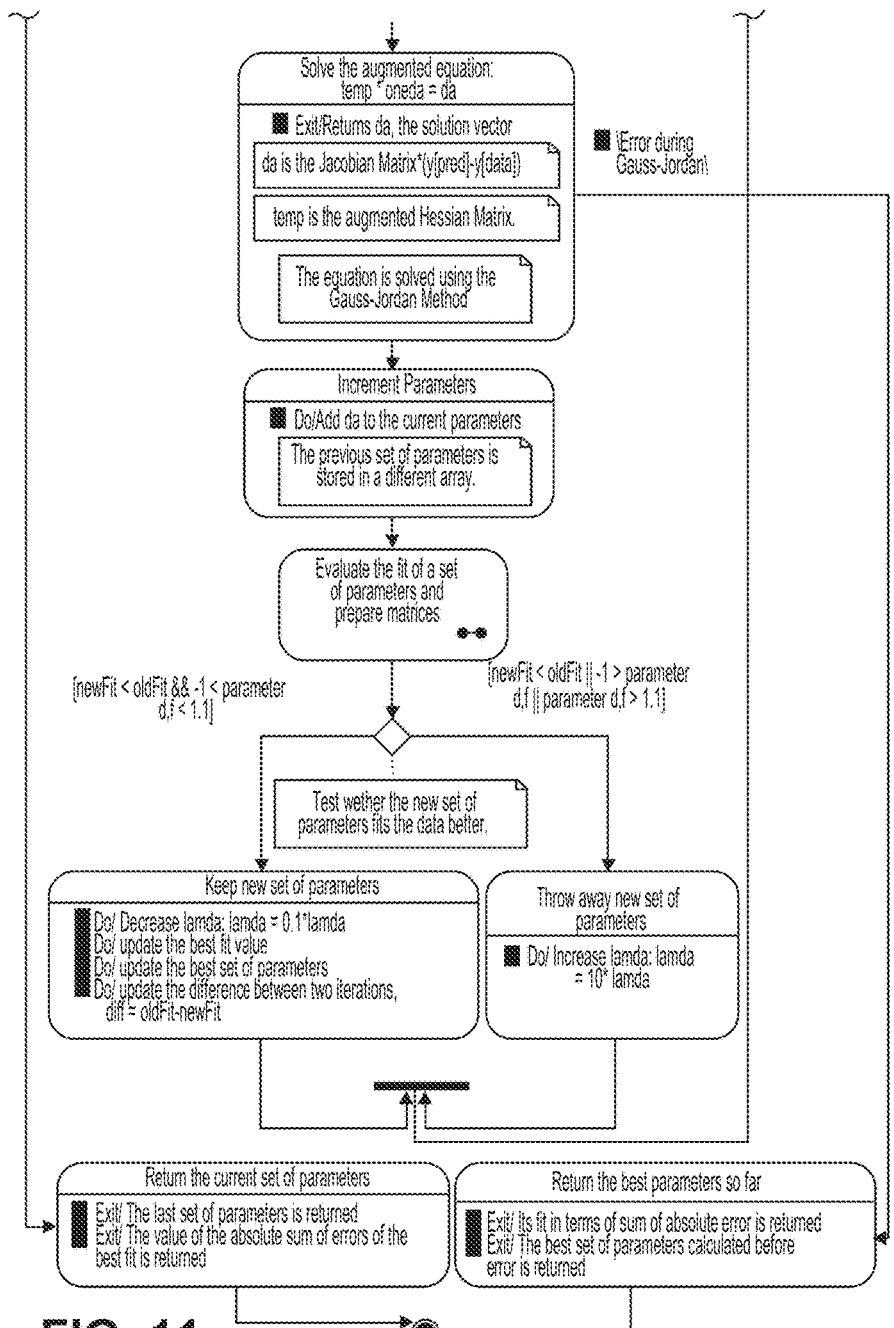

FIG. 11 illustrates a process flow of LM process 520 for a set of parameters according to the present invention. As explained above, the Levenberg-Marquardt method can behave either like a steepest descent process or like a Gauss-Newton process. Its behavior depends on a damping factor $\lambda$. The larger $\lambda$ is, the more the Levenberg-Marquardt algorithm will behave like the steepest descent process. On the other hand, the smaller $\lambda$ is, the more the Levenberg-Marquardt algorithm will behave like the Gauss-Newton process. In one aspect, $\lambda$, is initiated at 0.001. It should be appreciated that $\lambda$, may be initiated at any other value, such as from about 0.000001 to about 1.0.

As stated before, the Levenberg-Marquardt method is an iterative technique. According to one aspect, as shown in FIG. 11 the following is done during each iteration:
1. The Hessian Matrix (H) of the precedent approximation is calculated.
2. The transposed Jacobian Matrix ($J^T$) of the precedent approximation is calculated.
3. The distance vector (d) of the precedent approximation is calculated.
4. The Hessian Matrix diagonal is augmented by the current damping factor $\lambda$:

$$H_{aug} = H\lambda \quad (8)$$

5. Solve the augmented equation:

$$H_{aug}x = J^T d \quad (9)$$

6. The solution x of the augmented equation is added to the parameters of the function.
7. Calculate the distance between the new approximation and the curve.
8. If the distance with this new set of parameters is smaller than the distance with the previous set of parameters:
   The iteration is considered successful.
   Keep or store the new set of parameters.
   Decrease the damping factor $\lambda$, e.g., by a factor 10.
   If the distance with this new set of parameters is larger than the distance with the previous set of parameters:
   The iteration is considered unsuccessful.
   Throw away the new set of parameters.
   Increase the damping factor $\lambda$, e.g., by a factor of 10.

In one aspect, the LM process of FIG. 11 iterates until one of the following criteria is achieved:
1. It has run for a specified number, N, of iterations. This first criterion prevents the algorithm from iterating indefinitely. For example, in one aspect as shown in FIG. 10, the default iteration value N is 100. 100 iterations should be plenty for the algorithm to converge if it can converge. In general, N can range from fewer than 10 to 100 or more.
2. The difference of the distances between two successful iterations is smaller than a threshold value. e.g., 0.0001. When the difference becomes very small, the desired precision has been achieved and continuing to iterate is pointless as the solution won't become significantly better.
3. The damping factor $\lambda$, exceeds a specified value, e.g., is larger than $10^{20}$. When $\lambda$ becomes very large, the algorithm won't converge any better than the current solution, therefore it is pointless to continue iterating. In general, the specified value can be significantly smaller or larger than $10^{20}$.

According to another embodiment, the Levenberg-Marquardt method used is equivalent to the expressions specified in equation 10, below. Given a vector function f(z): $\mathfrak{R}^m \to \mathfrak{R}^n$ with initial condition $z_0$ and a precision level tol (e.g., set to $10^{-3}$ by default), equation 10 holds true. The function J(z) is defined as the Jacobian matrix of the function f(z). The variable maxiter is the maximum number of iterations (e.g., set to 100 by default). The variable $\lambda$ is the damping factor in the regression.

Equation 10 Levenberg-Marquardt Nonlinear Regression $\lambda = 0.01$ tol
iter = 0
z = $z_0$
while(($||f(z)||^2 >$ tol)and($\lambda \leq 10^{20}$)and(iter < maxiter))
  $z_{new} = z + ((J(z))^T \cdot J(z) + ((J(z))^T \cdot J(z)) \cdot (\lambda \cdot I))^{-1} \cdot f(z)$ if$\left( \dfrac{||f(z)||^2 - ||f(z_{new})||^2}{0.5 \cdot (z_{new} - z)^T \cdot (\lambda \cdot (z_{new} - z) - (J(z))^T \cdot f(z))} > 0 \right)$ z = $z_{new}$
  $\lambda = \lambda / 2$
  else
  $\lambda = 2 \lambda$
  end if
  iter = iter + 1
end while The inverse in equation 10 is taken with a QR decomposition. In one aspect, the QR decomposition is similar to the DGELS method of Anderson, E. (ed), "LAPACK Users' Guide," 3rd edition. Philadelphia, Pa.: Society for Industrial and Applied Mathematics, 1999. If an inverse cannot be determined, then λ is multiplied by 2 (or other value) and regression continues.

EXAMPLES

Case 1

This is an IQS (HEX channel) fluorescence data from CAP/CTM HIV Monitor assay. The assay design had a jump discontinuity after cycle 15. FIG. 12 shows the raw fluorescence data (dots) and corrected data (solid line). Table 4, below, shows the estimated coefficients and the corresponding confidence intervals. The $R^2$ for case 1 is greater than 0.99.

TABLE 4

Coefficients for case 1 illustration

| | Estimate | Asymptotic SE | CI |
|---|---|---|---|
| a | 2.31275 | 0.122562 | {2.06485, 2.56066} |
| b | 0.0252359 | 0.00549652 | {0.0141181, 0.0363536} |
| c | 96.3609 | 0.27873 | {95.7971, 96.9247} |
| d | 0.239047 | 0.00396729 | {0.231022, 0.247072} |
| e | 33.125 | 0.0631932 | {32.9971, 33.2528} |
| f | 0.758324 | 0.00009917 | {0.741941, 0.774706} |
| g | 31.9943 | 0.0357128 | {31.922, 32.0665} |
| h | 0.908027 | 0.0861226 | {0.733027, 1.00223} |

Case 2

This is a B19 Parvo-virus target channel (FAM Channel) without any real target being amplified. The assay design has a jump discontinuity after cycle 5. FIG. 13 shows the raw fluorescence data (dots) and corrected data (solid line). Table 5, below, shows the estimated model coefficients and their corresponding confidence interval. The $R^2$ for case 2 is 0.94.

TABLE 5

Coefficients for case 2 illustration

| | Estimate | Asymptotic SE | CI |
|---|---|---|---|
| a | 8.42742 | 0.0100461 | {8.4073, 8.44754} |
| b | 0.00685508 | 0.000274316 | {0.00630577, 0.00740439} |
| h | 0.442016 | 0.0171885 | {0.407597, 0.476435} |

Case 3

This is a target of a HBV High Pure (FAM channel). This assay does not have a jump discontinuity. The confidence interval of the coefficient h in this case will include zero. Hence, no correction of discontinuity is required. FIG. 14 shows the raw data (dots) and corrected data (solid line). Table 6, below, shows the estimated model coefficients and their corresponding confidence intervals. The $R^2$ for case 3 is greater than 0.99.

TABLE 6

Coefficients for case 3 illustration

| | Estimate | Asymptotic SE | CI |
|---|---|---|---|
| a | 3.11898 | 0.0996001 | {2.91861, 3.31935} |
| b | 0.00896466 | 0.00591903 | {−0.00294289, 0.0200722} |
| c | 23.0262 | 0.209375 | {22.605, 23.4474} |
| d | 0.350498 | 0.0578984 | {0.234021, 0.466974} |
| e | 26.6482 | 1.32442 | {23.9030, 29.3125} |
| f | 0.609921 | 0.0235677 | {0.562509, 0.657333} |
| g | 29.3633 | 0.302858 | {28.754, 29.9726} |
| h | −0.00380231 | 0.0809013 | {−0.166555, 0.15895} |

Case 4

This is a high concentration ($2.9 \times 10^{11}$ IU/ml) B19 Parvovirus sample (FAM channel). Although the assay design has a jump discontinuity after cycle 5, due to high copy number the discontinuity is not seen. The method described above is able to handle this case gracefully. FIG. 15 shows the raw data (dots) and corrected data (solid line). The confidence interval of the coefficient h in this case includes zero. Table 7, below, shows the estimated model coefficients and their corresponding confidence intervals. The $R^2$ for case 4 is greater than 0.99.

TABLE 7

Coefficients for case 4 illustration

| | Estimate | Asymptotic SE | CI |
|---|---|---|---|
| a | 9.28716 | 0.664719 | {7.9533, 10.621} |
| b | 0.0995382 | 0.0130251 | {0.0734015, 0.125675} |
| c | 73.394 | 1.01872 | {71.3498, 75.4382} |
| d | 0.156817 | 0.00342661 | {0.149941, 0.163693} |
| e | 14.6075 | 0.137083 | {14.3324, 14.8825} |
| f | 0.504019 | 0.0306282 | {0.443359, 0.566279} |
| g | 7.26305 | 0.212852 | {6.03593, 7.69017} |
| h | −0.166849 | 0.500549 | {−1.17127, 0.037576} |

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of automatically removing a step discontinuity in data representing a Polymerase Chain Reaction (PCR) growth process, the method comprising:
    detecting, with a PCR system, intensity values of signals generated using a biological and/or chemical reaction sample undergoing the PCR growth process, at a plurality of growth cycles of the PCR growth process;
    receiving, by a computer system communicatively coupled to the PCR system, a dataset representing the PCR growth process, the dataset including a plurality of data points, each data point having a pair of coordinate values, wherein the pair of coordinate values correspond to a cycle number of the PCR growth process and an intensity value of a signal generated using the biological and/or chemical reaction sample and detected by the PCR system after a growth cycle corresponding to the cycle number;
    calculating, by the computer system, a first approximation of a curve that fits the dataset by applying a first non-linear regression process to a first non-linear function to determine parameters of the first non-linear function, said parameters including a first step discontinuity parameter that represents a magnitude of the step discontinuity, the first non-linear function including the first step discontinuity parameter multiplying a step function;
    calculating, by the computer system, a second approximation of a curve that fits the dataset by applying a second regression process to a second non-linear function to determine parameters of the second non-linear function, said parameters of the second non-linear function including a second step discontinuity parameter that represents the magnitude of the step discontinuity, the second non-linear function including the second step discontinuity parameter multiplying a step function, wherein the second non-linear function is different from the first non-linear function;

determining, by the computer system, an information coefficient for each of the first and second approximations, each information coefficient indicating an accuracy of a fit of the corresponding approximation to the dataset;

selecting, by the computer system, one of the approximations based on the information coefficient, the selected approximation providing a best fit to the dataset;

determining, by the computer system, a confidence interval of the step discontinuity parameter for the selected approximation;

if the confidence interval does not include the value zero, replacing, by the computer system, a portion of the dataset with the selected approximation with the corresponding step discontinuity parameter set to zero, wherein the method is implemented in a computer system having a processor; and determining, by the computer system, a quantity of a target molecule in the biological and/or chemical reaction sample by determining a cycle threshold ($C_t$) value using the dataset.

2. The method of claim 1, wherein the first non-linear regression process is a Levenberg-Marquardt (LM) regression process and wherein the first non-linear function is a double sigmoid function.

3. The method of claim 2, wherein the double sigmoid function is of the form:

$$a + b \cdot x + \frac{c}{(1 + \exp(-d \cdot (x - e)))(1 + \exp(-f \cdot (x - g)))} + h \cdot (\text{UnitStep}(x) - \text{UnitStep}(x - cac)),$$

wherein UnitStep is of the form:

$$\text{UnitStep}(x) = \begin{cases} 1 & x \geq 0 \\ 0 & x < 0 \end{cases},$$

wherein h is the first step discontinuity parameter, and
wherein calculating the first approximation includes iteratively determining one or more of the parameters a, b, c, d, e, f, g and h of the double sigmoid function.

4. The method of claim 1, wherein the portion of the dataset replaced includes the portion of the dataset beginning with the first data point up to and including the data point at which the step discontinuity occurs.

5. The method of claim 1, further including, after the step of selecting, calculating a goodness of fit value for the selected approximation and continuing only if the goodness of fit value exceeds a threshold value.

6. The method of claim 5, wherein the portion of the dataset replaced includes the data point after the data point at which the step discontinuity occurs.

7. The method of claim 1, wherein determining the information coefficient for each of the first and second approximations includes calculating an Akaike Information Coefficient (AIC) value for each of the first and second approximations.

8. The method of claim 7, further including subtracting a bias value from the AIC value calculated for the second approximation.

9. The method of claim 7, wherein selecting one of the approximations based on the information coefficient includes selecting the approximation having the lowest AIC value.

10. The method of claim 1, wherein the dataset represents a growth curve for a kinetic Polymerase Chain Reaction (PCR) process, and wherein the pair of coordinate values represent an accumulation of amplified polynucleotide and a cycle number.

11. The method of claim 10, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

12. A computer-readable medium including code for controlling a processor to automatically remove a step discontinuity in a dataset representing a growth curve, the code including instructions to:

receive a dataset obtained by measuring a growth process of a biological and/or chemical reaction sample, the dataset including a plurality of data points, each data point having a pair of coordinate values;

calculate a first approximation of a curve that fits the dataset by applying a first non-linear regression process to a first non-linear function to determine parameters of the first non-linear function, said parameters including a first step discontinuity parameter that represents a magnitude of the step discontinuity, wherein the first non-linear function includes the first step discontinuity parameter multiplying a step function;

calculate a second approximation of a curve that fits the dataset by applying a second regression process to a second non-linear function to determine parameters of the second non-linear function, said parameters of the second non-linear function including a second step discontinuity parameter that represents the magnitude of the step discontinuity, wherein the second non-linear function includes the second step discontinuity parameter multiplying a step function, and wherein the second non-linear function is different from the first non-linear function;

determine an information coefficient for each of the first and second approximations, each information coefficient indicating an accuracy of a fit of the corresponding approximation to the dataset;

select one of the approximations based on the information coefficient, the selected approximation providing a best fit to the dataset;

determine a confidence interval of the step discontinuity parameter for the selected approximation;

if the confidence interval does not include the value zero, replace a portion of the dataset with the selected approximation with the corresponding step discontinuity parameter set to zero; and determine a quantity of a target molecule in the biological and/or chemical reaction sample by determining a cycle threshold (CO value using the dataset.

13. The computer readable medium of claim 12, wherein the first non-linear regression process is a Levenberg-Marquardt (LM) regression process and wherein the first non-linear function is a double sigmoid function, wherein the double sigmoid function is of the form:

$$a + b \cdot x + \frac{c}{(1 + \exp(-d \cdot (x - e)))(1 + \exp(-f \cdot (x - g)))} +$$
$$h \cdot (\text{UnitStep}(x) - \text{UnitStep}(x - cac)),$$

wherein UnitStep is of the form:

$$\text{UnitStep}(x) = \begin{cases} 1 & x \geq 0 \\ 0 & x < 0 \end{cases},$$

wherein h is the first step discontinuity parameter, and
wherein calculating the first approximation includes iteratively determining one or more of the parameters a, b, c, d, e, f, g and h of the double sigmoid function.

14. The computer readable medium of claim 12, wherein the portion of the dataset replaced includes the portion of the dataset beginning with the first data point up to and including the data point at which the step discontinuity occurs.

15. The computer readable medium of claim 12, wherein the instructions to determine the information coefficient for each of the first and second approximations includes instructions to calculate an Akaike Information Coefficient (AIC) value for each of the first and second approximations, the code further including instructions to subtract a bias value from the AIC value calculated for the second approximation.

16. A kinetic Polymerase Chain Reaction (PCR) system, comprising:
a kinetic PCR analysis module that generates a PCR dataset representing a kinetic PCR amplification curve by detecting intensity values of signals generated using a biological and/or chemical reaction sample undergoing a PCR growth process at a plurality of growth cycles of the PCR growth process, said dataset including a plurality of data points, each having a pair of coordinate values, wherein the pair of coordinate values correspond to a cycle number of the PCR growth process and an intensity value of a signal generated using the biological and/or chemical reaction sample and detected by the kinetic PCR analysis module after a growth cycle corresponding to the cycle number; and
an intelligence module adapted to process the PCR dataset to automatically remove a step discontinuity in the dataset, by:
calculating a first approximation of a curve that fits the dataset by applying a first non-linear regression process to a first non-linear function to determine parameters of the first non-linear function, said parameters including a first step discontinuity parameter that represents a magnitude of the step discontinuity, wherein the first non-linear function includes the first step discontinuity parameter multiplying a step function;
calculating a second approximation of a curve that fits the dataset by applying a second regression process to a second non-linear function to determine parameters of the second non-linear function, said parameters of the second non-linear function including a second step discontinuity parameter that represents the magnitude of the step discontinuity, wherein the second non-linear function includes the second step discontinuity parameter multiplying a step function, and wherein the second non-linear function is different from the first non-linear function;
determining an information coefficient for each of the first and second approximations, each information coefficient indicating an accuracy of a fit of the corresponding approximation to the PCR dataset;
selecting one of the approximations based on the information coefficient, the selected approximation providing a best fit to the PCR dataset;
determining a confidence interval of the step discontinuity parameter for the selected approximation;
if the confidence interval does not include the value zero, replacing a portion of the dataset with the selected approximation with the corresponding step discontinuity parameter set to zero; and
determining a quantity of a target molecule in the biological and/or chemical reaction sample by determining a cycle threshold ($C_t$) value using the dataset.

17. The system of claim 16, wherein the first non-linear regression process is a Levenberg-Marquardt (LM) regression process and wherein the first non-linear function is a double sigmoid function, wherein the double sigmoid function is of the form:

$$a + b \cdot x + \frac{c}{(1 + \exp(-d \cdot (x - e)))(1 + \exp(-f \cdot (x - g)))} +$$
$$h \cdot (\text{UnitStep}(x) - \text{UnitStep}(x - cac)),$$

wherein UnitStep is of the form:

$$\text{UnitStep}(x) = \begin{cases} 1 & x \geq 0 \\ 0 & x < 0 \end{cases},$$

wherein h is the first step discontinuity parameter, and
wherein calculating the first approximation includes iteratively determining one or more of the parameters a, b, c, d, e, f, g and h of the double sigmoid function.

18. The system of claim 16, wherein determining the information coefficient for each of the first and second approximations includes calculating an Akaike Information Coefficient (AIC) value for each of the first and second approximations, wherein the intelligence module is further adapted to subtract a bias value from the AIC value calculated for the second approximation.

19. The system of claim 16, wherein the intelligence module is further adapted to, after selecting, calculating a goodness of fit value for the selected approximation and continuing only if the goodness of fit value exceeds a threshold value.

20. The method of claim 1, further comprising:
determining, by the computer system, an efficiency of the PCR growth process based on the $C_t$ value.

* * * * *